United States Patent [19]

Christensen et al.

[11] 4,273,709
[45] Jun. 16, 1981

[54] PROCESS FOR THE PREPARATION OF THIENAMYCIN AND INTERMEDIATES

[75] Inventors: Burton G. Christensen, Scotch Plains; Ronald W. Ratcliffe, Matawan; Thomas N. Salzmann, North Plainfield, all of N.J.

[73] Assignee: Merck & Co., Inc., Rahway, N.J.

[21] Appl. No.: 59,842

[22] Filed: Jul. 23, 1979

[51] Int. Cl.³ .................. C07D 205/08; C07D 487/04
[52] U.S. Cl. ............................... 260/239 A; 560/148; 260/245.2 T
[58] Field of Search .................................... 260/239 A

[56] References Cited

U.S. PATENT DOCUMENTS 4,210,661  7/1980  Ponsford et al. ............... 260/239 A
4,223,038  9/1980  Smale ............................. 260/239 A

FOREIGN PATENT DOCUMENTS 2811514  9/1978  Fed. Rep. of Germany ... 260/239 AL

OTHER PUBLICATIONS

Durst, et al., J. Amer. Chem. Soc. 94, 9261 (1972).

*Primary Examiner*—Mark L. Berch
*Attorney, Agent, or Firm*—James A. Arno; Hesna J. Pfeiffer

[57] ABSTRACT

Disclosed is a process for the total synthesis of thienamycin from 4-allylazetidinone (IIIa) via

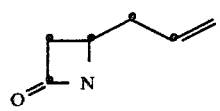

IIIa L-aspartic acid (III):

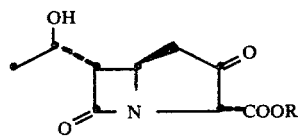

III

R=H, blocking group or salt cation.

4 Claims, No Drawings

PROCESS FOR THE PREPARATION OF THIENAMYCIN AND INTERMEDIATES

BACKGROUND OF THE INVENTION

This invention relates to the total synthesis of the known antibiotic thienamycin (I).

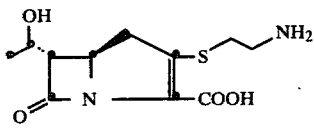

Starting from 4-allylazetidinone (IIIa), the synthesis proceeds via intermediates III and IV.

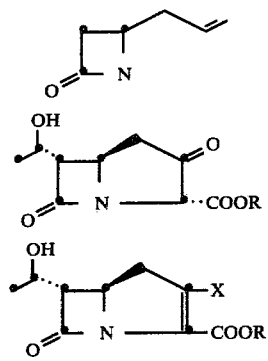

wherein X is a conventional leaving group and R is hydrogen, a conventional, readily removable protecting group or a salt cation. The details of the total synthesis are given below.

DETAILED DESCRIPTION OF THE INVENTION

The process of the present invention may conveniently be summarized by the following reaction diagram:

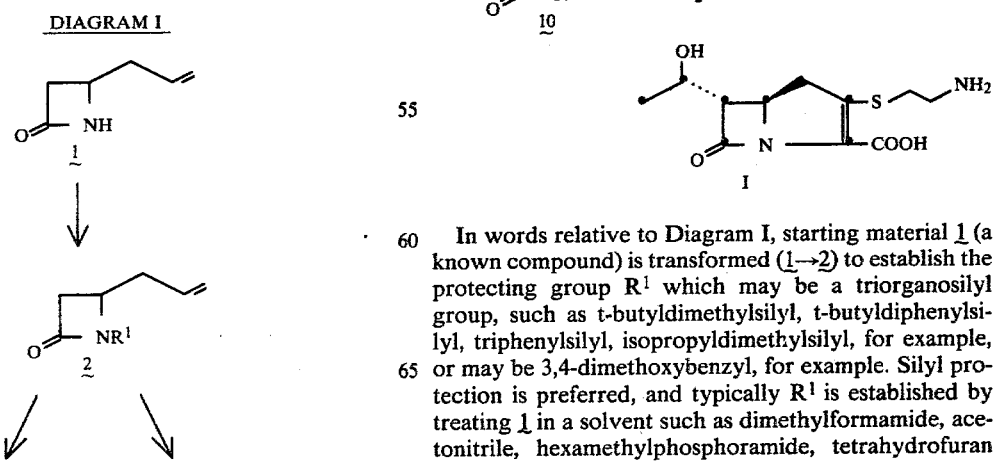

In words relative to Diagram I, starting material 1 (a known compound) is transformed (1→2) to establish the protecting group $R^1$ which may be a triorganosilyl group, such as t-butyldimethylsilyl, t-butyldiphenylsilyl, triphenylsilyl, isopropyldimethylsilyl, for example, or may be 3,4-dimethoxybenzyl, for example. Silyl protection is preferred, and typically $R^1$ is established by treating 1 in a solvent such as dimethylformamide, acetonitrile, hexamethylphosphoramide, tetrahydrofuran and the like with a silylating agent such as t-butyldimethylchlorosilane, t-butyldiphenylchlorosilane, triphenylchlorosilane, and the like at a temperature of from −20° to 25° C. for from 0.5 to 24 hours in the presence of a base such as triethylamine, diisopropylethylamine, or imidazole.

The alkylation 2→3 is accomplished by treating 3 in a solvent such as tetrahydrofuran, dimethoxyethane, diethylether, hexamethylphosphoramide, at a temperature of from −100° to −20° C. with a strong base such as lithium diisopropylamide, lithium hexamethyldisilazide, lithium 2,2,6,6-tetramethylpiperidide, potassium hydride or the like followed by the addition of an equivalent to 10 fold excess of acetaldehyde. This reaction gives a mixture of isomers from which the desired trans-R form can be conveniently separated by chromatography or crystallization.

Intermediate 2 may proceed directly to 3, as indicated above, or it may take the circuitous path via 3a. The direct acetylation, to 3a is accomplished by treating 3 with two or more equivalents of a base such as lithium diisopropylamide, lithium hexamethyldisilazide, lithium 2,2,6,6-tetramethylpiperidide, in a solvent such as tetrahydrofuran, diethylether, or dimethoxyethane, for example, at a temperature of from −100° to −20° C. with an acylating agent such as N-acetyl imidazole or the like. Addition of the 3 plus base mixture to the acylating agent is preferred.

The reduction, 3a→3, is accomplished by contacting the ketone with a reducing agent such as potassium tri(sec-butyl)borohydride, lithium tri(sec-butyl)borohydride, sodium borohydride, sodium tris(methoxyethoxy)aluminum hydride, lithium aluminum hydride or the like in a solvent such as diethylether, tetrahydrofuran, toluene or the like at a temperature of from −20° to 25° C. The reaction can conveniently be conducted in the presence of an added complexing salt such as potassium iodide, magnesium bromide or the like.

In a similar manner, unresolved 3 (3') may be oxidized to 3a for reduction to 3 as indicated above:

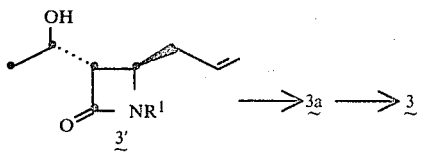

The oxidation (3'→3a) is accomplished with an oxidizing agent such as dipyridine chromium (VI) oxide, trifluoroacetic anhydride-dimethylsulfoxide-triethylamine, pyridinium dichromate, acetic anhydride-dimethylsulfoxide in a solvent such as methylene chloride, acetonitrile, or the like at a temperature of from −78° to 25° C. for from 5 minutes to 5 hours.

The oxidation 3→4 is accomplished by treating 3 in a solvent such as methylenechloride, methanol chloroform, or the like, with an oxidizing agent such as Ozone, or the like, at a temperature of from −100° to 0° C. for from 0.1 to 4 hours, followed by treating the crude product with an oxidizing agent such as m-chloroperchenzoic acid, hydrogen peroxide, peracetic acid, or the like, at a temperature of from 0° C. to 100° C. for from 1 to 100 hours.

Intermediate species 4 is racemic. Resolution to obtain the R, 3S, 4R-isomer is conveniently conducted at this point. Such resolution may be achieved by any of a variety of known procedures, such as: physical separation via crystallization, chromatography of the diasteomeric salts formed on reaction of 4 with an appropriate optically active amine such as bracine, ephedsine, strychnine, morphine, or the like.

The addition 4→5 is accomplished by treating 4 with 1,1'-carbonyldimidazole, or the like, in a solvent such as tetrahydrofuram, dimethoxyethane, or the like, at a temperature of from 0° to 50° C., followed by the addition of 1.1 to 3.0 equivalent of $(R^7O_2CCH_2CO_2)_2Mg$, at a temperature of from 0° to 50° C. for from 1 to 48 hours. $R^7$ is a readily removable carboxyl protecting groups such as p-nitrobenzyl, benzyl, or the like.

Removal of protecting group $R^1$ (5→6) is accomplished by acidic aqueous hydrolysis of 5 in a solvent such as methanol, ethanol, tetrahydrofuran, dioxane, or the like, in the presence of an acid such as hydrochloric, sulfuric, acetic or the like at a temperature of from 0° to 100° C. for from 2 to 18 hours.

The diazo species 7 is prepared from 16 by treating 6 in a solvent such as $CH_3CN$, $CH_2Cl_2$, THF, or the like, with an azide such as p-carboxybenzenesulfonylazide, toluenesulfonylazide, methanesulfonylazide, or the like, in the presence of a base such as triethylamine, pyridine, $(C_2H_5)_2NH$, or the like, for from 1 to 50 hours at 0°–25° C.

Cyclization (7→8) is accomplished by treating 7 in a solvent such as benzene, toluene, THF, or the like, at a temperature of from 50°–110° C. for from 1–5 hours in the presence of a catalyst such as bis (acetylacetonato)-Cu(II) [Cu(acac)$_2$], CuSO$_4$, Cu powder, Rh(OAc)$_2$, or Pd(OAC)$_2$. Alternatively, the cyclization may be accomplished by irradiating 7 through a pyrex filter (a wave length greater than 300 nm) in a solvent such as benzene, CCl$_4$, diethylether, or the like, at a temperature of from 0°–25° C. for from 0.5 to 2 hours. ["OAc"-=acetate.]

Establishment of leaving group X (8→9) is accomplished by acylating the keto ester 18 with an acylating agent $R^\circ X$ such as p-toluenesulfonic acid anhydride, p-nitrophenylsulfonic acid anhydride, 2,4,6-triisopropylphenylsulfonic acid anhydride, methanesulfonic acid anhydride, toluenesulfonyl chloride, p-bromophenylsulfonyl chloride, or the like wherein X is the corresponding leaving group such as toluene sulfonyloxy, p-nitrophenylsulfonyloxy, methanesulfonyloxy, p-bromophenylsulfonyloxy and other leaving groups which are established by conventional procedures and are well known in the art. Typically, the above acylation to establish leaving groups X is conducted in a solvent such as methylene chloride, acetonitrile or dimethylformamide, in the presence of a base such as diisopropylethylamine, triethylamine, 4-dimethylamino-pyridine or the like at a temperature of from −20° to 40° C. for from 0.5 to 5 hours. The leaving group X of intermediate can also be halogen. The halogen leaving group is established by treating 18 with a halogenating agent such as $\phi_3PCl_2$, $\phi_3PBr_2$, $(\phi O)_3PBr_2$, oxalyl chloride or the like in a solvent such as CH$_2$Cl$_2$, CH$_3$CN, THF, or the like in the presence of a base such as diisopropylethylamine, triethylamine, or 4-dimethylaminopyridine or the like. [$\phi$=phenyl.]

The reaction 9→10 is accomplished by treating 9 in a solvent such as dioxane, dimethylformamide, dimethylsulfoxide, acetonitrile, hexamethylphosphoramide, or the like in the presence of an approximately equivalent to excess of the mercaptan reagent HSCH$_2$CH$_2$NHR$^8$ wherein R$^8$ is hydrogen or a readily removable N- protecting group such as p-nitrobenzyloxycarbonyl, o-nitrobenzyloxycarbonyl, or the like in the presence of a base such as sodium hydrogen carbonate, potassium carbonate, triethylamine, diisopropylethylamine, or the like at a temperature of from −40° to 25° C. for from 1 to 72 hours. The mercaptan reagent, $HSCH_2CH_2NHR^8$, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours.

The final deblocking step $\underline{10} \rightarrow I$ is accomplished by conventional procedures such as hydrolysis or hydrogenation. Typically $\underline{10}$ in a solvent such as dioxane-water-ethanol, tetrahydrofuran-aqueous dipotassium hydrogen phosphate-isopropanol or the like is treated under a hydrogen pressure of from 1 to 4 atmospheres in the presence of a hydrogenation catalyst such as palladium on charcoal, palladium hydroxide, or the like at a temperature of from 0° to 50° C. for from 0.5 to 4 hours to provide I.

In the foregoing word description of the above schematic reaction diagram for the total synthesis of thienamycin, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation.

EXAMPLE 1

Preparation of 1-(t-Butyldimethylsilyl)-4-(prop-2-one)-azetidin-2-one

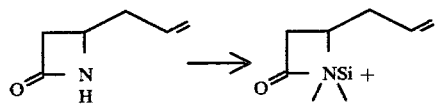

t-Butyldimethylchlorosilane (7.51 g, 49.8 mmol) is added in one portion to an ice-cold, stirring solution of 4-(prop-2-ene)-azetidin-2-one (5.26 g, 47.4 mmol) and triethylamine (5.04 g 49.8 mmol) in anhydrous dimethylformamide (100 ml). A voluminous white precipitate forms almost immediately. The reaction mixture is stirred at 0°–5° for 1 hour and then allowed to warm to room temperature. Most of the solvent is removed under vacuum to give a residue which is partitioned between diethyl ether (250 ml) and water. The ethereal phase is washed with 2.5 N hydrochloric acid (50 ml), water (3×50 ml), and brine, dried with magnesium sulfate, filtered and evaporated under vacuum to provide an oil which is purified either by vacuum distillation or chromatography on silica gel (20% ether in petroleum ether) to yield 1-(t-Butyldimethylsilyl-4-(prop-2-ene)-azetidin-2-one. n.m.r.($CnCl_3$)δ4.8–6.0(3H, m, olefinic),δ3.5(1H, m, H4),δ3.03(1H,dd,J=15,5.2H3x), δ2.56(1H,dd,J=15, 2.8,H2β),δ1.8-2.8(2H, m, allylic), δ0.9(9H,S),δ0.2(6H,S).

EXAMPLE 2

1-(t-Butyldimethylsilyl)-3-(1-hydroxyethyl)-4-(prop-2-ene)-azetidin-2-one

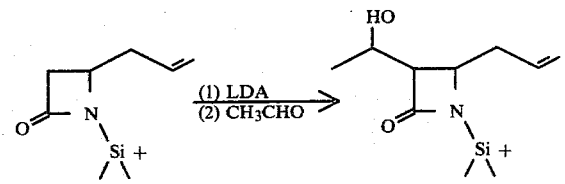

n-Butyllithium in hexane (26.25 mmol) is added slowly by syringe to a solution of diisopropylamine (26.25 mmol) in anhydrous tetrahydrofuran (100 ml) at −78° C. The resulting solution is stirred for 15 min prior to the addition of a solution of 1-(t-butyldimethylsilyl)-4-(prop-2-ene)-azetidin-2-one (25.0 mmol) in anhydrous tetrahydrofuran (25 ml). After stirring for 15 min at −78° C., acetaldehyde (75 mmol) is added by syringe and the resulting solution is stirred at −78° C. for 5 min. Saturated aqueous ammonium chloride solution (15 ml) is added by syringe and the reaction mixture is allowed to warm to room temperature, then diluted with ether (250 ml) and washed with 2.5 N hydrochloric acid solution (2×5 ml), water (100 ml) and brine and dried over magnesium sulfate. Solvents are removed in vacuo and the semi-solid residue is chromatographed on silica gel (1:1, ether:petroleum ether). The first product to elute is the cis R compound (688 mg) n.m.r. ($CDCl_3+D_2O$)δ4.8 - 6.2 (3H, m, olefinic),δ4.2 (1H, dq J=6.5, 3.7, H-8),δ3.75(1H, ddd, J=5.5, 5, 4.8, H-5)δ3.28 (H, dd, J=5.5, 3.7, H-6),δ2.2-3.0 (2H, m, allyl),δ1.35 (3H, d, J=6.5, C$\underline{H}_3$-CHOH),δ1.0(9H, S,±Si-),δ0.3(6H, S, (C$\underline{H}_3$)$_2$Si). The second fraction is a mixture of the trans R and S products (5.56 g). Crystallization of this material from petroleum ether gives the pure trans R material, m.p. 81°–82° C. IR (CHCl$_3$) 3400, 2920, 2850, 1723 cm$^{-1}$; n.m.r. (CDCl$_3$+D$_2$O)δ 4.9-6.2 (3H, m, olefinic), δ 4.1 (1H, dq, J=7.0, 6.8, H8), δ3.66 (1H, ddd, J=11, 4.5, 3.0, H5), δ 2.9 (1H, dd, J=6.8, 3.0, H6)δ1.8-2.8 (2H, m, allyl), δ1.26 (3H, d, J=7.0, C$\underline{H}_3$-), δ1.0 (9H, S, ±Si), δ 0.28 (6H, 2S, (C$\underline{H}_3$)$_2$Si).

EXAMPLE 3

1-(t-Butyldimethylsilyl)-3-(1-oxoethyl)-4-(prop-2-ene)-azetidin-2-one

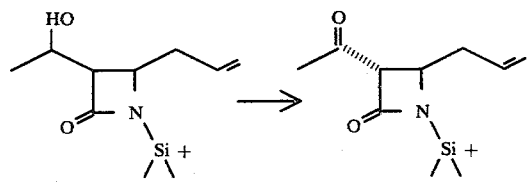

A. Trifluoroacetic anhydride (7.5 mmol) is added dropwise by syringe to a solution of dimethylsulfoxide (10 mmol) in anhydrous methylene chloride (15 ml) at −78° C. The resulting mixture is stirred at −78° C. for 20 min. during which time a white precipitate forms. A solution of 1-(t-butyldimethylsilyl)-3-(1-hydroxyethyl)-4-(prop-2-ene)-azetidin-2-one (5.0 mmol) in methylene chloride (15 ml) is added by syringe and the resulting solution is stirred at −78° C. for 30 min. Triethylamine (14 mmol) is added by syringe and the cooling bath is removed. After an additional 1 hr., the reaction mixture is diluted with methylene chloride (100 ml), washed with water (50 ml) and brine and dried over magnesium sulfate. Removal of solvents in vacuo yields an oil which is chromatographed on silica gel (2:1, petroleum ehter:ether) to yield 1-(t-butyldimethylsilyl-3-(1-oxoethyl)-4-(prop-2-ene)-azetidin-2-one. I.R. (CHCl₃) 2925, 2855, 1734, 1705 cm⁻¹; n.m.r. (CDCl₃) δ 4.8-6.1 (3H, m, olefinic) δ3.8-4.2 (2H, overlapping multiplets, H5, H6), δ 2.0-2.9 (2H, m, allylic, δ2.3

$$\text{(3H, S, CH}_3\text{—}\overset{\overset{\displaystyle O}{\|}}{\text{C}}\text{)}$$

δ 0.96 (9H, S, ±Si-), δ 0.25 (6H, 2S, (C<u>H</u>₃)₂Si). Mass spectrum m/e 267(m+)252,226,210.

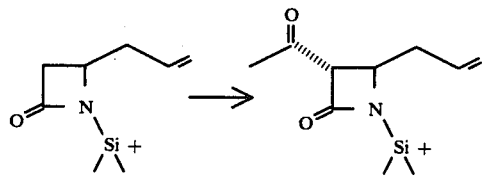

B. n-Butyllithium in hexane (4.10 mmol) is added by syringe to a solution of diisopropylamine (4.10 mmol) in anhydrous tetrahydrofuran (16 ml) at −78° C. The resulting solution is stirred at −78° C. for 15 min. prior to the addition of a solution of 1-(t-butyldimethylsilyl)-4-(prop-2-ene)-azetidin-2-one (2.0 mmol) in anhydrous tetrahydrofuran (2 ml). After an additional 15 min. at −78° C., the reaction mixture is added via a Teflon tube to a mixture of N-acetylimidazole (4.1 mmol) in anhydrous tetrahydrofuran (16 ml) at −78° C. The resulting yellow reaction mixture is stirred at 31 78° C. for 15 min, then quenched by addition of saturated aqueous ammonium chloride solution (10 ml). The reaction mixture is diluted with ether (100 ml) and washed with 2.5 N hydrochloric acid solution (25 ml) water (25 ml) and brine. The organic phase is dried over magnesium sulfate and concentrated in vacuo to yield an oil. This material is chromatographed on silica gel (2:1 petroleum ether:ether) to yield 1-(t-butyldimethylsilyl)-3-(1-oxoethyl)-4-(prop-2-ene)-azetidin-2-one.

EXAMPLE 4

1-(t-Butyldimethylsilyl)-3-(1-hydroxyethyl)-4-(prop-2-ene)-azetidin-2-one

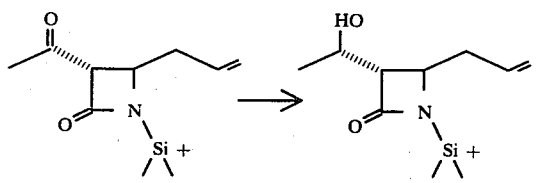

K-Selectride (potassium tri-(sec)-butylborohydride) in tetrahydrofuran (4.8 mmol) is added by syringe to a mixture of potassium iodide (2.0 mmol) and 1-(t-butyldimethylsilyl)-3-(1-oxoethyl)-4-(prop-2-ene)-azetidin-2-one (2.0 mmol) in anhydrous ether (20 ml) at room temperature. The resulting mixture is stirred at room temperature for 2.5 hours, then quenched by addition of glacial acetic acid (9.6 mmol). The resulting mixture is diluted with ethylacetate (100 ml) and filtered through celite. Removal of solvents in vacuo gives an oil which is chromatographed on silica gel (1:1 ether:petroleum ether) to yield 1.90 g (95%) of 1-(t-Butyldimethylsilyl)-3-(1-hydroxyethyl)-4-(prop-2-ene)-azetidin-2-one as a white solid. N.M.R. examination of this material indicates the R/S ratio to be >5/1. The R isomer is isolated by crystallization from petroleum ether.

EXAMPLE 5

1-(t-Butyldimethylsilyl)-3-(1-hydroxyethyl)-4-(carboxymethyl)-azetidin-2-one.

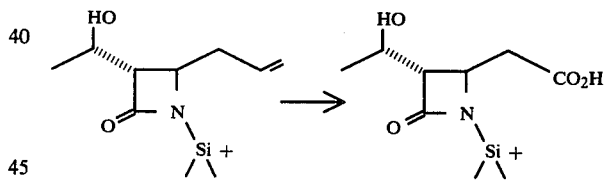

A solution of 1-(t-butyldimethylsilyl)-3-(1-hydroxyethyl)-4-(prop-2-ene)-azetidin-2-one (3.0 mmol) in dry methylene chloride (30 ml) is cooled to −78° C. (dry ice-acetone) and a stream of ozone is bubbled through until the reaction mixture becomes blue. The ozone flow is then stopped and the reaction is purged by bubbling through nitrogen until the blue color disappears. Solid m-chloroperbenzoic acid (3.0 mmol) is added and the cold bath is removed. When the reaction mixture reaches room temperature, the flask is fitted with a reflux condenser and the mixture is heated at reflux for three days. Removal of solvents in vacuo gives a white solid which is chromatographed on silica gel (2% glacial acetic acid in methylene chloride) to yield 663 mg (77%) of 1-(t-Butyldimethylsiyl-3-(1-hydroxyethyl)-4-(carboxymethyl)-azetidin-2-one. n.m.r. (CDCl₃+D₂O) δ 3.6-4.3 (2H, m), δ 2.98 (1H, dd, J=7, 2.1), δ 2.7 (2H, d of ABq, —CH₂CO₂H), δ 1.29 (3H, d, J=6), δ 0.95 (9H, S), δ 0.25 (6H, S).

EXAMPLE 6

(3S, 4R)-1-(t-Butyldimethylsilyl)-3-[(R)-1-hydroxyethyl]-4-(3-p-nitrobenzyloxycarbonyl-2-oxopropyl)-azetidin-2-one

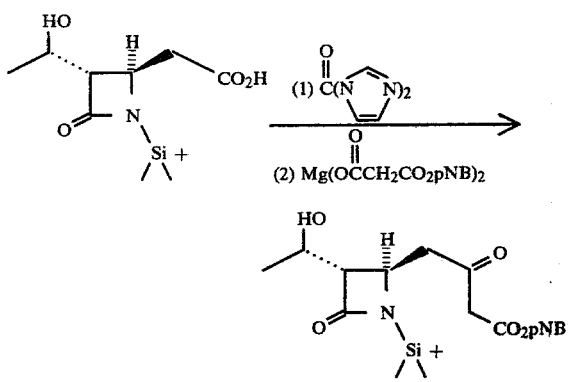

1,1'-Carbonyldimidazole (1.10 mmol) is added in one portion to a solution of (3S, 4R)-1-(t-butyldimethylsilyl-3-[(R)-1-hydroxyethyl]-4-carboxymethyl-azetidin-2-one (1.0 mmol) in anhydrous tetrahydrofuran (5 ml) at room temperature. The resulting solution is stirred at room temperature for 6 hours. In a second flask, magnesium ethoxide (5 mmol) is added in one portion to a solution of the mono-p-nitrobenzyl ester of malonic acid (10 mmol) in anhydrous tetrahydrofuran (25 ml). The resulting mixture is stirred at room temperature for 1 hr, then the tetrahydrofuran is removed at the pump and the gummy residue is triturated with ether to yield the magnesium salt as an off-white solid. (1.1 mmol) of this magnesium salt is then added to the first reaction flask and the resulting mixture is stirred at room temperature for 18 hrs. The reaction mixture is then poured into 50 ml of ether, washed with 0.5 N hydrochloric acid solution (20 ml), water (20 ml), saturated aqueous sodium bicarbonate solution (20 ml), brine and dried over magnesium sulfate. Removal of solvents in vacuo gives an oil which is chromatographed on silica gel (ether) to yield (3S,4R)-1-(t-butyldimethylsilyl)-3-[(R)-1-hydroxyethyl]-4-(3-p-nitrobenzyloxycarbonyl-2-oxopropyl)-azetidin-2-one. n.m.r. (CDCl$_3$-H$_2$O) δ 8.24, 8.10, 7.52, 7.38(2H, AB, aromatic), δ 5.26 (2H, S, —CH$_2$-Ar), δ 3.5-4.2 (2H, m, H-5, H-8), δ 2.6-3.3

(3H, m, H—, —CH$_2$—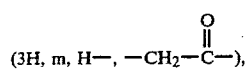—),

δ 1.3 (3H, d, J=6.6, CH$_3$—) δ 0.98 (9H, S, ±Si-) δ 0.25 (6H, S, (CH$_3$)$_2$Si<).

EXAMPLE 7

(3S,4R)-3-[(R)-1-hydroxyethyl]-4-(3-p-nitrobenzyloxycarbonyl-2-oxopropyl)-azetidin-2-one

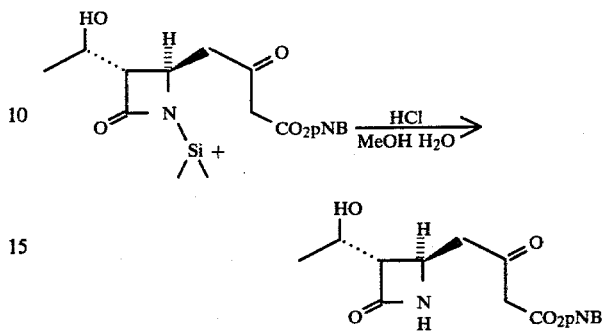

A solution of (3S, 4R)-1-(t-butyldimethylsilyl)-3-[(R)-1-hydroxyethyl]-4-(3-p-nitrobenzyloxycarbonyl-2-oxopropyl)-azetidin-2-one (1.0 mmol) in 20 ml of 9:1 (v/v) methanol-water is cooled to 0° C. Concentrated hydrochloric acid (0.34 ml) is added and the resulting solution is stirred at 0° C. for 15 min., then allowed to warm to room temperature. After 2.5 hrs, at room temperature the reaction mixture is diluted with ethyl acetate (25 ml), washed with water (10 ml) and brine, dried over magnesium sulfate and concentrated in vacuo to yield (3S, 4R)-3-[(R)-1-hydroxyethyl]-4-(3-p-nitrobenzyloxycarbonyl-2-oxopropyl)-azetidin-2-one.

EXAMPLE 8

Preparation of (3S,4R)-3-[(R)-1-hydroxyethyl]-4-[3-(4-nitrobenzyl)oxycarbonyl-2-oxo-3-diazopropyl]azetidin-2-one

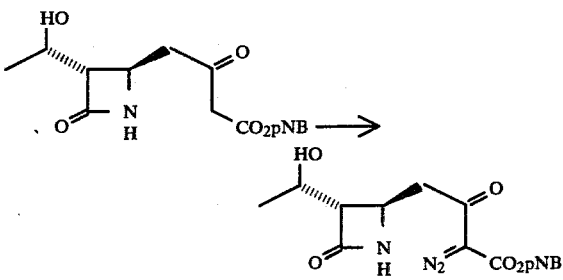

Triethylamine (263 mg, 2.6 mmol) is added by syringe to a mixture of (3S,4R)-3-[(R)-1-hydroxyethyl]-4-[3-(4-nitrobenzyl) oxycarbonyl-2-oxopropyl]azetidin-2-one (253 mg, 0.72 mmol) and p-carboxybenzene sulfonylazide (196 mg, 0.84 mmol) in dry acetonitrile (6 ml) at 0° C. When addition is complete the cooling bath is removed and the reaction mixture is stirred at room temperature for 1 hour. The mixture is then diluted with ethyl acetate (50 ml) and filtered. The filtrate is concentrated in vacuo and the residue is chromatographed on a short silica gel column (ethyl acetate) to yield 222 mg, (81% overall from (3S, 4R)-1-(t-butyldimethyl-silyl)-3-[(R)-1-(t-butyl dimethylsilyloxy)ethyl]-4-[3-(4-nitrobenzyl)oxycarbonyl-2-oxopropyl]azetidin-2-one) of (3S,4R)-3-(R)-1-hydroxyethyl)-4-[3-(4-nitrobenzyl)oxycarbonyl-2-oxo-3-diazopropyl]azetidin-2-one as a white solid m.p. (dec.) 163° C. IR(CHCl$_3$, CM$^{-1}$) 3410, 2132, 1756, 1718, 1650, 1350, 1280, 1120; n.m.r.

(CDCl₃)δ7.9(2d-aromatic, 4),δ5.4(s,2), δ6.2(brs,1),δ4.1(m,2),δ2.6-3.6(m,4),δ1.32(d,3,J=6.2).

EXAMPLE 9

Preparation of (5R,6S) p-Nitrobenzyl 6-[(R) 1-hydroxyethyl]-1-azabicyclo [3.2.0]heptan-3,7-dione-2-carboxylate

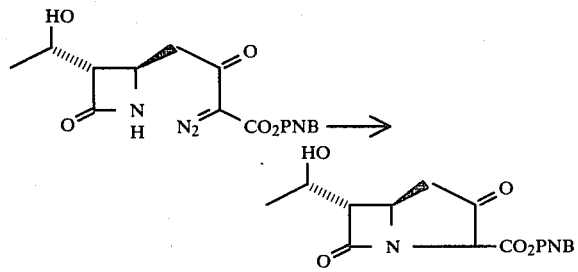

A suspension of (3S,4R)-3-[(R)-1-hydroxyethyl]-4-[3-(4-nitrobenzyl)oxycarbonyl-2-oxo-3-diazopropyl]azetidin-2one (56.4 mg, 0.15 mmol) and rhodium (II) acetate (0.1 mg) in dry benzene (3 ml) is deoxygenated by bubbling through nitrogen for 10 minutes. The mixture is then heated to 78° C. for 1 hour. During heating the solid starting material gradually goes into solution. The mixture is then cooled, filtered to remove the catalyst, and the filtrate is concentrated in vacuo to yield (5R, 6S) p-nitrobenzyl 6-[(R)-1-hydroxyethyl]-1-azabicyclo[3.2.0]heptan-3,7-dione-2-carboxy-late, 51 mg. (98%) as a colorless oil which slowly crystallized at room temperature (22° C.). Physical Properties:

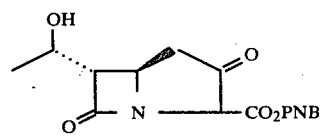

PNB = p-nitrobenzyl n.m.r.: (300 MHz, CDCl₃)δ8.26, 7.54 (aromatic, 4), 5.29 (AB,2), 4.77 (s,1), 4.32(dg, I,J=6.6,7), 4.16(ddd, 1,J=7,7.5,2.2), 3.21(dd,1,J=7,2.2), 2.94(dd,2,J=19.5,7) 2.50(dd,1,J= 19.5,7.5), 2.2(brs,1), 1.37(d,3,J=6.6).

I.R.: (CHCl₃,CM⁻¹) 1770, 1758, 1610, 1522, 1353 m.p. 110°-111° C.

EXAMPLE 10

Preparation of p-Nitrobenzyloxycarbonylaminoethanethiol

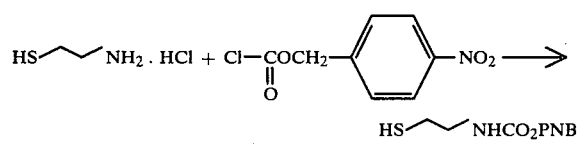

To 600 ml diethyl ether (Et₂O) - 75 ml H₂O in an ice bath with stirring is added 3.2 g cysteamine hydrochloride (mw=114; 28.1 mmole). A solution of 7.14 g NaHCO₃ (mw=84; 85 mmole) in 75 ml H₂O is added. The ice bath is removed, and at room temperature a solution of 6.75 g p-nitrobenzylchloroformate (mw=216; 31.3 mmole) in 270 ml Et₂O is added dropwise over a period of one hour. After 10 additional minutes, the layers are separated. The ether layer is extracted with 150 ml 0.25 N HCl, and then with 200 ml brine. Each aqueous layer is then backwashed successively with 100 ml Et₂O. The combined Et₂O layers are dried over anhydrous MgSO₄, filtered, and concentrated under a N₂ stream. The crystalline residue is slurried in a small amount of ether, filtered, and the pale yellow crystals are dried under high vacuum to give 4.7 g. p-nitrobenzyloxycarbonylaminoethanethiol (65% yield). NMR (CDCl₃): 8.18 (d, J=8 Hz, aromatic protons ortho to nitro), 7.47 (d, J=8 Hz, aromatic protons meta to nitro), 5.27 (—NH—), 5.20 (s, —CH₂—NH—), 2.67 (m, —CH₂—SH), 1.35 (t, J=8.5 Hz, —SH) in ppm downfield from TMS. IR (CHCl₃ solution): carbonyl- 1725 cm⁻¹. M.S.: molecular ion-256, (M-47) at 209, (M-136) at 120, +CH₂φpNO₂ at 136.

EXAMPLE 11

Preparation of (5R,6S) p-Nitrobenzyl 3-[2-(p-nitrobenzyloxycarbonyl)amine ethylthio]-6-[(R)-1-hydroxyethyl]-1-azabicyclo [3,2,0]-hept-2-en-7-one-2-carboxylate

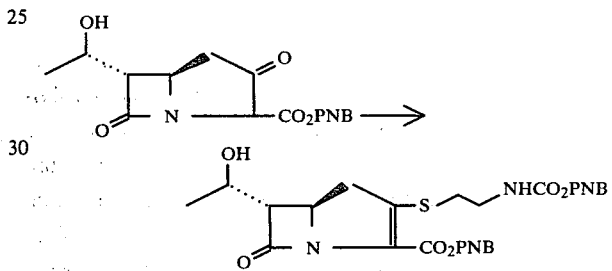

(5R,5S) p-Nitrobenzyl 6-[(R)1-hydroxyethyl]-1-azabicyclo [3,2,0]heptan-3,7-dione-2-carboxylate (51 mg, 0.147 mmol) is dissolved in acetonitrile (3 ml) and the resulting solution is cooled to 0° C. Diisopropylethylamine (22 mg, 0.17 mmol) is added by syringe and the resulting solution is stirred at 0° C. for 1 minute prior to the addition of a solution of freshly recrystallized p-toluene sulfonic anhydride (51 mg., 0.156 mmol) in dry acetonitrile (1 ml). The resulting solution is stirred at 0° C. for 1 hour to provide (5R, 6S)p-nitrobenzyl 3-(p-toluenesulfonyloxy)-6-[(R)-1-hydroxyethyl]-1-azabicyclo[3.2.0]hept-2-en-7-one-2-carboxylate, then cooled to —25° C. Diisopropylethylamine (80.5 mg, 0.624 mmol) is added by syringe followed shortly thereafter by a solution of N-p-nitrobenzyloxycarbonylcysteamine (40 mg, 0.156 mmol) in 1 ml of dry acetonitrile. The reaction mixture is then stored in a refrigerater for 70 hr. The mixture is diluted with 25 ml of ethyl acetate washed with brine and dried over magnesium sulfate. Solvents are removed in vacuo to yield a yellow oil which is chromatographed on a silica gel plate (ethyl acetate, R$_f$=0.4) to yield (5R, 6S) p-nitrobenzyl-3-[2-(p-nitrobenzyloxycarbonyl)amino ethylthio]-6-[(R)-1-hydroxyethyl]-1-azabicyclo [3,2,0]-hept -2-en-7-dione-2-carboxylate as a yellow solid, m.p. 167°-169° C. IR(-Nujol mull) 1773 and 1690 cm⁻¹; n.m.r. (DCDl₃)δ7.54-8.26 (overlapping ABq, 4),δ5.40(ABq,2),δ5.22(s,2),δ4.27(m, 2),δ3.47 (m),δ3.23(dd,1),δ3.14(dd,1)δ3.40(dd,1),δ3.04(m,2),δ1.3-7(d,3).

EXAMPLE 12

Preparation of Thienamycin

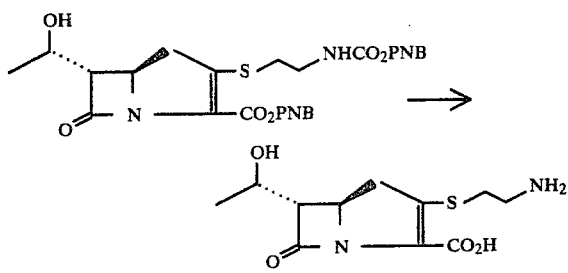

A mixture of N-p-nitrobenzyloxycarbonyl thienamycin p-nitrobenzyl ester (10 mg, 0.017 mmol) and 10% Pd/C-Bolhofer type in tetrahydrofuran (2 ml), 0.1 M dipotassium hydrogen phosphate solution (1.4 ml) and 2-propanol (0.2 ml) is hydrogenated at 40 psi on the Parr shaker for 30 minutes. The mixture is then filtered and the catalyst is washed with water (3×3 ml). The combined filtrate and washings are extracted with ethyl acetate-ethyl ether then concentrated to ~3 ml and lyophilized. The resulting white powder is identical to natural thienamycin in all respects.

What is claimed is:

1. The compound of the formula

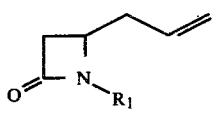

wherein $R^1$ is triloweralkylsilyl, wherein the alkyl moieties have from 1 to 6 carbon atoms.

2. The compound selected from the group consisting of

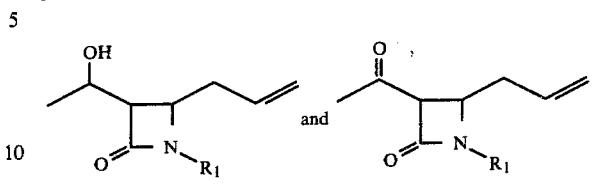

wherein $R^1$ is hydrogen or triloweralkylsilyl, wherein the alkyl moieties individually have 1 to 6 carbon atoms.

3. A compound of the formula:

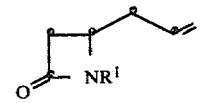

wherein $R^1$ is selected from the group consisting of t-butyldimethylsilyl, t-butyldiphenylsilyl, triphenysilyl and isopropyldimethylsilyl.

4. A compound selected from the group consisting of:

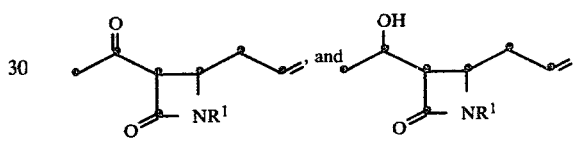

wherein $R^1$ is selected from the group consisting of hydrogen, t-butyldimethylsilyl, t-butyldiphenylsilyl, triphenylsilyl and isopropyldimethylsilyl.

* * * * *